(12) United States Patent
Fuchs et al.

(10) Patent No.: US 7,179,875 B2
(45) Date of Patent: Feb. 20, 2007

(54) METHOD FOR PRODUCING WATER-ABSORBENT RESINS

(75) Inventors: Eberhard Fuchs, Frankenthal (DE); Hans Martan, Frankenthal (DE); Gerhard Nestler, Vienna (AT); Klaus Joachim Mueller-Engel, Stutensee Blankenloch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/485,484

(22) PCT Filed: Aug. 2, 2002

(86) PCT No.: PCT/EP02/08646

§ 371 (c)(1), (2), (4) Date: Jul. 20, 2004

(87) PCT Pub. No.: WO03/014172

PCT Pub. Date: Feb. 20, 2003

(65) Prior Publication Data

US 2004/0236049 A1   Nov. 25, 2004

(30) Foreign Application Priority Data

Aug. 3, 2001 (DE) .................. 101 38 150

(51) Int. Cl.
 *C08F 220/06*  (2006.01)

(52) U.S. Cl. .............. 526/317.1; 526/83; 526/84; 95/210; 95/213; 203/8; 560/208; 562/512.2; 562/532; 562/598; 562/600

(58) Field of Classification Search .......... 560/208; 562/512.2, 532, 600, 598; 526/317.1, 84, 526/83; 95/210, 213; 203/8
See application file for complete search history.

(56) References Cited

U.S. PATENT DOCUMENTS

| | | | |
|---|---|---|---|
| 3,868,417 A | | 2/1975 | Willersinn et al. |
| 4,828,652 A | * | 5/1989 | Schropp .................... 203/38 |
| 5,426,221 A | | 6/1995 | Willersinn |
| 5,482,597 A | * | 1/1996 | Herbst et al. .............. 203/38 |
| 5,705,688 A | | 1/1998 | Fauconet et al. |
| 5,817,865 A | * | 10/1998 | Machhammer et al. ..... 560/208 |
| 6,207,022 B1 | * | 3/2001 | Dockner et al. ............ 203/38 |
| 6,228,227 B1 | * | 5/2001 | Herbst et al. .............. 203/59 |
| 6,395,140 B1 | * | 5/2002 | Herbst et al. ............... 203/8 |
| 6,444,744 B1 | * | 9/2002 | Fujimaru et al. .......... 524/556 |
| 6,498,272 B1 | * | 12/2002 | Schroder ................... 562/600 |
| 6,518,452 B1 | * | 2/2003 | Aichinger et al. ......... 560/205 |
| 6,679,939 B1 | * | 1/2004 | Thiel et al. ................ 95/210 |
| 6,740,779 B1 | * | 5/2004 | Tenten et al. .............. 562/598 |
| 2001/0050216 A1 | * | 12/2001 | Kroker et al. ................ 203/6 |
| 2003/0092938 A1 | * | 5/2003 | Nishimura et al. ........ 562/600 |

FOREIGN PATENT DOCUMENTS

| | | |
|---|---|---|
| DE | 196 34 614 | 3/1998 |
| EP | 0 727 408 | 8/1996 |
| EP | 0 770 592 | 5/1997 |
| FR | 2 753 445 | 3/1998 |

* cited by examiner

*Primary Examiner*—Helen L. Pezzuto
(74) *Attorney, Agent, or Firm*—Oblon, Spivak, McClelland, Maier & Neustadt, P.C.

(57) ABSTRACT

In a process for preparing water-absorbent resins based on acrylic acid, crude acrylic acid is firstly isolated from the reaction gases from the catalytic gas-phase oxidation of propane, propylene and/or acrolein. This is treated with an aldehyde scavenger and pure acrylic acid is separated by distillation from the treated crude acrylic acid, and this pure acrylic acid can be subjected directly to a free-radical polymerization.

17 Claims, 1 Drawing Sheet

METHOD FOR PRODUCING WATER-ABSORBENT RESINS

BACKGROUND OF THE INVENTION

1. Field of the Invention

Figure 1:
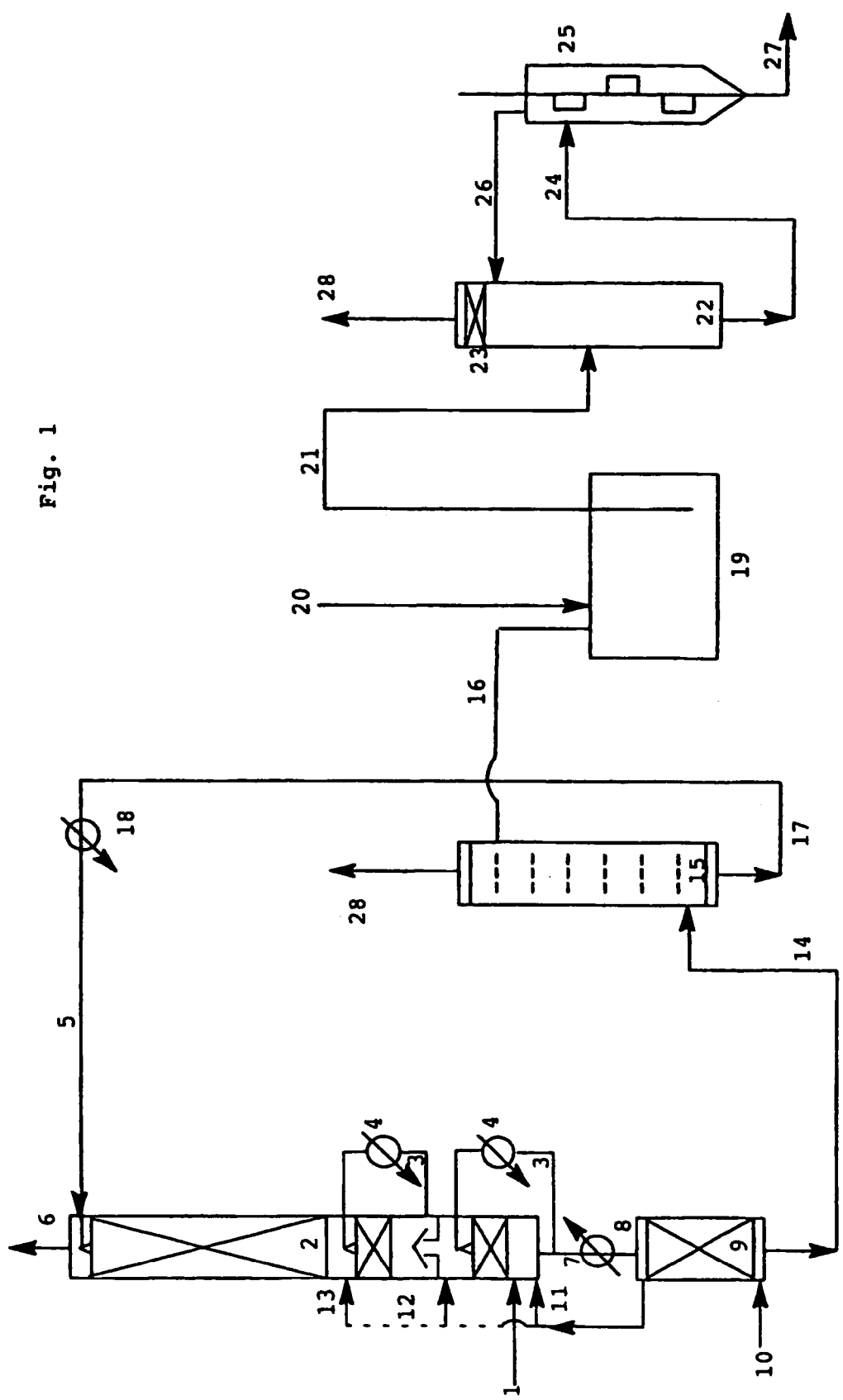

Water-absorbent resins based on acrylic acid, in particular those known as superabsorbents, are widely used in, for example, hygiene articles.

2. Description of the Background

It is known that acrylic acid can be prepared by heterogeneously catalyzed gas-phase oxidation of propane, propylenene (and/or acrolein) by means of molecular oxygen over solid catalysts. The gas-phase oxidation of propane, propylene and/or acrolein forms the desired acrylic acid together with by-products, in particular in the form of carbonyl compounds, e.g. aldehydes such as benzaldehyde, furfurals, propionaldehyde etc., and also formic acid and maleic acid or maleic anhydride, whose presence has an adverse effect on the polymerization if the acrylic acid is used for preparing superabsorbents. Aldehydes hinder the polymerization of the acrylic acid and also lead to discolored polymers. The presence of maleic anhydride in the polymerization leads to formation of undesired copolymers which influence the properties of the desired polymers. Contamination by carboxylic acids which are not capable of polymerization, e.g. formic acid, are particularly disadvantageous when the polyacrylic acids prepared by polymerization are used in hygiene articles which come into contact with human skin, since these carboxylic acids cause extreme skin irritation. The presence of oligomeric acrylic acids, e.g. diacrylic, triacryilic or tetraacrylic acid, is troublesome because the oligomeric acrylic acid present dissociates during the thermal treatment of the polyacrylic acid and liberates acrylic acid, which likewise causes extreme skin irritation.

In the preparation and/or isolation of acrylic acid, use is generally made of process polymerization inhibitors such as phenothiazine, hydroquinone or hydroquinone monomethyl ether to suppress undesirable premature polymerization, particularly at elevated temperatures. Undesired polymer formation leads to deposits on heat exchanger surfaces and column trays and also to blockage of lines, pumps, valves etc. Since the process polymerization inhibitors, which have an excellent inhibiting action, naturally also retard intended preparation of polyacrylic acid, they subsequently have to be removed again from the acrylic acid obtained and be replaced by storage polymerization inhibitors which have less of an inhibiting action.

To remove or reduce the amounts of the abovementioned by-products and impurities, multistage distillation and/or extraction and/or crystallization steps are generally employed in the prior art. Acrylic acid which is obtainable in this way and is suitable for preparing absorbent resins is generally referred to as pure acrylic acid. Thus, EP 0 754 671 discloses a distillation process for purifying acrylic acid prepared by catalytic oxidation of propylene, in particular to remove maleic anhydride. EP 0 727 408 discloses a two-stage distillation of crude acrylic acid. The fraction taken off at the top, which comprises formic acid and acetic acid, is esterified to make use of the acetic acid.

DE 2 241 714 discloses a process for separating acrylic acid from the reaction gases from the oxidation of propylene or acrolein by means of countercurrent absorption, with acetic acid and some water being stripped from the resulting absorption solution by means of inert gases. DE 4 308 087 describes a process for separating acrylic acid from the reaction gases from the catalytic oxidation of propylene and/or acrolein by countercurrent absorption using a mixture of diphenyl ether, biphenyl and dimethyl o-phthalate.

DE 196 34 614 discloses a process for separating off pure (meth)acrylic acid by distillation in a distillation apparatus which comprises a thin film evaporator, a condenser and a connection comprising an impingement device between thin film evaporator and condenser.

SUMMARY OF THE INVENTION

It is an object of the present invention to provide a process for preparing water-absorbent resins, in which acrylic acid is separated in a technically simple manner from the reaction gases from the catalytic gas-phase oxidation of propane, propylene and/or acrolein and which gives an acrylic acid which can be used directly without further purification for preparing the water-absorbent resins.

We have found that this object is achieved by a process for preparing water-absorbent resins, which comprises
a) obtaining crude acrylic acid by either
   a1) absorbing acrylic acid from the reaction gases from the catalytic gas-phase oxidation of propane, propylene and/or acrolein in an absorption liquid and isolating crude acrylic acid from the absorption liquid laden with acrylic acid,
   or
   a2) separating a crude acrylic acid fraction from the reaction gases by fractional condensation and, if appropriate, subjecting the fraction to purification by crystallization,
b) treating the crude acrylic acid with an aldehyde scavenger,
c) separating pure acrylic acid from the treated crude acrylic acid by distillation, and
d) subjecting the pure acrylic acid, if appropriate after partial neutralization, if desired in admixture with further ethylenically unsaturated monomers, to a free-radical polymerization.

DETAILED DESCRIPTION OF THE PREFERRED EMBODIMENTS

The pure acrylic acid obtained in step c) generally contains less than 1 ppm of process polymerization inhibitor such as phenothiazine, less than 5 ppm of formic acid, less than 5 ppm of aldehyde and less than 100 ppm of diacrylic acid.

The oxidation of propane, propylene and/or acrolein to form acrylic acid in the gas phase is carried out in a manner known per se. The feed, which may have been mixed with an inert diluent gas, is passed in admixture with oxygen over at least one heterogeneous catalyst, generally a mixed oxide catalyst comprising transition metals, e.g. molybdenum, vanadium, tungsten and/or iron, at elevated temperatures, usually from 200 to 400° C., and at atmospheric or superatmospheric pressure and is thus converted into acrylic acid by oxidation. The reaction can be carried out in one or two stages. In a two-stage reaction, the propylene is oxidized to acrolein in a first stage and the acrolein is oxidized to acrylic acid in a second stage. Heterogeneous catalysts used in the first stage are preferably oxidic multicomponent catalysts based on the oxides of molybdenum, bismuth and iron, while preferred catalysts in the second stage are appropriate catalysts based on the oxides of molybdenum and vanadium.

The conversion of propane, propylene and/or acrolein into acrylic acid is strongly exothermic. The feed stream is therefore advantageously diluted with an inert diluent gas, e.g. atmospheric nitrogen, carbon dioxide, methane and/or steam. Although the type of reactors used is not subject to any particular restriction, use is advantageously made of shell-and-tube heat exchangers charged with the oxidation catalyst(s), since in these the major part of the heat liberated in the reaction can be removed by convection and radiation at the cooled walls of the tubes. The reaction gases obtained in the single—or two-stage catalytic gas-phase oxidation usually comprises acrylic acid together with unreacted propane, propylene and/or acrolein, steam, carbon monoxide, carbon dioxide, nitrogen, oxygen, acetic acid, propionic acid, formaldehyde, further aldehydes and maleic acid or maleic anhydride. The reaction gases typically comprise:

| | |
|---|---|
| acrylic acid | from 1 to 30% by weight |
| propylene | from 0.05 to 1% by weight |
| acrolein | from 0.01 to 2% by weight |
| propane | from 0.01 to 2% by weight |
| steam | from 1 to 30% by weight |
| carbon oxides | from 0.05 to 15% by weight |
| nitrogen | from 0 to 90% by weight |
| oxygen | from 0.05 to 10% by weight |
| formic acid | from 0.01 to 1% by weight |
| acetic acid | from 0.05 to 2% by weight |
| propionic acid | from 0.01 to 2% by weight |
| aldehydes | from 0.01 to 3% by weight |
| maleic anhydride | from 0.01 to 0.5% by weight |

Crude acrylic acid having an acrylic acid content of usually at least 99% by weight is firstly isolated from the reaction gases. Methods of isolating crude acrylic acid from the reaction gases are known per se. In one embodiment of the process of the present invention, acrylic acid is absorbed from the reaction gases by means of an absorption liquid. Suitable absorption liquids are liquids in which acrylic acid has a pronounced solubility, e.g. liquids which have a boiling point higher than that of acrylic acid (hereinafter, "high-boiling liquid") and whose boiling point is preferably above 160° C. (at 1 atm). Possible high-boiling liquids are, for example, biphenyl, diphenyl ether, dimethyl phthalate, ethylhexanoic acid, N-methylpyrrolidone, paraffin fractions and mixtures thereof. Alternatively, oligomeric acrylic acids, e.g. mixtures comprising diacrylic, triacrylic and tetraacrylic acids, can be used as high-boiling liquid. Biphenyl, diphenyl ether, dimethyl o-phthalate and mixtures thereof are preferred, in particular mixtures comprising from 25 to 30% by weight of biphenyl and from 70 to 75% by weight of diphenyl ether together with, based on the mixture, from 0.1 to 25% by weight of dimethyl o-phthalate.

Water is also a suitable absorption liquid.

The absorption liquid is brought into intimate contact with the reaction gases in an appropriate manner. For this purpose, the reaction gases are advantageously passed through an absorption column in countercurrent flow to the descending absorption liquid. Examples of absorption columns which can be used are columns containing random or ordered packing, valve tray columns of bubble cap tray columns.

The reaction gases, which are generally at a temperature of from 200 to 400° C., are preferably cooled to a suitable absorption temperature of, for example, from 100 to 180° C. before being introduced into the absorption column. Cooling of the reaction gases to the absorption temperature can be carried out by indirect cooling, e.g. by means of a heat exchanger. However, this cooling is preferably carried out by direct contact with a cooling liquid, preferably in a spray scrubber. The cooling liquid is advantageously largely separated off again in a separator, cooled and recirculated before the reaction gases enter the absorption column. The cooling liquid is preferably identical to the liquid which is used for the subsequent absorption of the acrylic acid from the reaction gases.

The absorption liquid laden with acrylic acid generally comprises not only acrylic acid but also volatile impurities such as water, acrolein, formaldehyde and also formic acid and acetic acid. Secondary components such as water, acrolein, formaldehyde and the aceteic and formic acids can be at least partly removed by stripping with a stripping gas, particularly when using a high-boiling liquid as absorption liquid. For this purpose, the absorption liquid laden with acrylic acid is passed through a desorption column in countercurrent to a stripping gas, e.g. nitrogen or air. The amount of stripping gas required depends, in particular, on the desorption temperature, which is advantageously 20–50° C. higher than the absorption temperature; the stripping step is preferably carried out at the same pressure as the absorption step. The amount of stripping gas is preferably, based on the amount of reaction gas, from 5 to 25% by volume. The desorption column can be, for example, a column containing random or ordered packing, a valve tray column or a bubble cap tray column.

The cooling liquid and/or the absorption liquid usually contain an amount of, for example, from 0.01 to 1% by weight of at least one process polymerization inhibitor such as phenothiazine, phenolic compounds such as hydroquinone, hydroquinone monomethyl ether, p-nitrosophenol, tert-butylphenols, 1-oxyl-2,2,6,6-tetramethylpiperidin-4-ol or mixtures thereof. Use is frequently made of phenothiazine in an amount of from 0.01 to 1% by weight.

Crude acrylic acid is then isolated from the absorption liquid laden with acrylic acid. When using a high-boiling liquid as absorption liquid, the crude acrylic acid is usually separated off by rectification. The separation by rectification is advantageously carried out under reduced pressure, e.g. from 0.04 to 0.1 bar, for example in a packed column or tray column. A polymerization inhibitor is advantageously added at the top or in the upper region of the rectification column. The crude acrylic acid can be taken off at the top, but it is preferably taken off at a side offtake in the upper region of the rectification column, with small amounts of impurities having boiling points lower than that of acrylic acid, e.g. water and acetic acid, being taken off at the top of the column. The high-boiling liquid obtained after the crude acrylic acid has been separated off is advantageously recirculated and reused for absorption. It is sometimes advantageous for all or part of the residue which comprises mainly the high-boiling liquid to be treated thermally at above 180° C. before it is recirculated to the absorption column, so that ester-like oligomeric acrylic acids present as impurities are dissociated and the resulting acrylic acid is distilled off together with the high-boiling liquid. The maleic acid and maleic anhydride which are still present can be removed in a customary manner, e.g. by extraction with water, before the high-boiling liquid is reused.

If water is used as absorption liquid for absorbing the acrylic acid from the reaction gases, the crude acrylic acid is advantageously isolated from the initially obtained aqueous acrylic acid solution by extraction with an extractant and subsequent distillation of the extract. The extractant should have a high partition coefficient for acrylic acid and a low solubility in water and has to form an azeotrope with water. It is possible to use extractants which have boiling points lower than that of acrylic acid, e.g. ethyl acetate, butyl acetate, ethyl acrylate, 2-butanone or mixtures thereof, or extractants having boiling points higher than that of acrylic acid, e.g. t-butyl phosphate, isophorone or aromatic hydrocarbons. To carry out the extraction, the aqueous acrylic acid solution is advantageously passed through an extraction column in countercurrent to the chosen extractant.

Crude acrylic acid is then separated from the extract by distillation. The way in which the distillation is carried out depends on whether the extractant used has a boiling point higher or lower than that of acrylic acid. When using an extractant having a boiling point lower than that of acrylic acid, the extract is, for example, fed to a solvent separation column in which the extractant and residual amounts of water are distilled off via the top. The bottom fraction from the solvent separation column is then fed to a low boiler column in which impurities having boiling points lower than that of acrylic acid, e.g. acetic acid, are separated off at the top and crude acrylic acid is obtained as bottom fraction.

Instead of isolating crude acrylic acid from the reaction gases by absorption in an absorption liquid, it is also possible to recover crude acrylic acid by fractional condensation of the reaction gases, if appropriate with subsequent purification by crystallization.

To carry out the fractional condensation, the reaction gases, whose temperature has preferably been reduced to, for example, from 100 to 180° C., by direct cooling using a cooling liquid, is advantageously introduced into the lower region of the column containing separation-active internals and is allowed to ascent within the column. A crude acrylic acid fraction can be taken off as intermediate-boiling fraction via an appropriately installed collection tray. Such a process is described, for example, in DE 19740253 or DE 19740252. A process polymerization inhibitor, e.g. one of those mentioned above, is generally introduced into the column.

The crude acrylic acid fraction obtained in the fractional condensation can be passed to a crystallization for further purification. The crystallization process is not subject to any restrictions. If a crystallization is employed, it is advantageously carried out as a suspension crystallization.

The crude acrylic acid obtained by the above method is treated with an aldehyde scavenger. The aldehyde scavenger can be added directly into a pipe by means of which the crude acrylic acid is passed to further work-up or can be added in a residence vessel in which the crude acrylic acid is subjected to temporary storage before it is passed to further work-up.

Suitable aldehyde scavengers include all compounds which convert the aldehydes present in the crude acrylic acid essentially quantitatively into compounds having a boiling point higher than that of acrylic acid. Nitrogen compounds having at least one primary amino group are particularly suitable for this purpose. Examples which may be mentioned are aminoguanidine salts, hydrazine, alkylhydrazines and arylhydrazines, carboxylic acid hydrazides or aminophenols. Among these, particular preference is given to aminoguanidine hydrogen carbonate. The aldehyde scavenger is preferably used in an excess over the aldehyde present in the crude acrylic acid, e.g. in an amount of from 1.5 to 2.5 mol per mole of aldehyde. The reaction with the aldehyde scavenger can be carried out at from 15 to 50° C., preferably from 20 to 30° C. A reaction time of from 10 minutes to 72 hours, preferably from 2 to 50 hours, is usually employed. If aminoguanidine hydrogen carbonate is used as aldehyde scavenger, this firstly reacts too give off carbon dioxide and form aminoguanidine hydrogen acrylate. This reacts with the aldehyde groups of the aldehydes present to the corresponding iminoguanidine derivatives or their rearrangement products which are obtained as high boilers in the subsequent distillation. Treatment with the aldehyde scavenger allows the residual aldehyde content of the crude acrylic acid, expressed as furfural, to be reduced to below 20 ppm, in particular below 5 ppm, particularly preferably below 3 ppm.

Pure acrylic acid is then separated off from the crude acrylic acid which has been treated in this way by distillation. In this context, "separation by distillation" is meant in its broadest sense and encompasses both a simple distillation, i.e. a distillation in which essentially no mass transfer occurs between condensate and vapor, and a rectification in which part of the condensate is conveyed in countercurrent to the ascending vapor. It is a critical feature of the present invention that no fraction boiling at a lower temperature than the pure acrylic acid fraction is isolated, which leads to a simplification of the process and in general saves a distillation column ("low boiler column"). An advantageous method is to separate the treated crude acrylic acid thermally into vapor comprising acrylic acid and a residue and to condense the vapor quantitatively to obtain pure acrylic acid.

The thermal separation is preferably carried out by simple distillation, i.e. essentially without reflux of condensate. Accordingly, use is advantageously made of a distillation column without separation-active internals, i.e. a hollow column-like or tower-like structure which is generally made of stainless steel. To prevent droplets of crude acrylic acid from being entrained in the vapor comprising acrylic acid, the column is advantageously provided with a droplet precipitator of conventional construction, e.g. in the form of knitted wire packing which has a large internal surface area and can be made of, for example, chromium-nickel steels, aluminum, polypropylene, polytetrafluoroethylene or the like, or in the form of a bed of random packing elements or ordered packing, e.g. a stack of spaced, corrugated metal sheets arranged parallel to the longitudinal axis of the column, having a small height of, for example, from 20 to 100 cm.

The temperature at the bottom is usually from about 65 to 130° C., preferably from 70 to 100° C., and the column pressure is usually from 50 to 120 mbar. Heating at the bottom of the column is provided by an external or internal circulation vaporizer, preferably a Robert vaporizer or a forced circulation decompression vaporizer. In vaporizers of the Robert type, a heating unit comprising vertical boiler tubes is accommodated in a cylindrical vaporizer body. The crude acrylic acid is present in the interior of the boiler tubes. Circulation in the tubes is effected by the rising bubbles of vapor. To recirculate the liquid which has been conveyed upward, one or more downcomers are installed in the heating unit.

Apart from the above-described heating at the bottom, the column is preferably not actively heated; however, the wall of the column is preferably insulated to avoid excessive heat loss by radiation. The absence of column heating (apart from the heating at the bottom) results in droplets of crude acrylic acid entrained in the vapor comprising acrylic acid not being heated on their way through the gas space of the column and their size not being reduced by evaporation of volatile constituents. The entrained droplets, which retain their size or are enlarged by coagulation, can then readily be held back during passage of the vapor comprising acrylic acid through a droplet precipitator.

Apart from the wall of the column, the remaining parts of the plant which come into contact with the vapor comprising acrylic acid, in particular the pipes through which the vapor comprising acrylic acid is conveyed before it is condensed, are provided with auxiliary heating to avoid undesirable premature condensation. Thus, the pipes can, for example, be configured as double-wall tubes through whose annular space between outer and inner wall a heating medium is circulated. Alternatively, it is possible to provide a tube through which a heating medium flows and which is in heat-conductive contact with the pipe conveying the vapor comprising acrylic acid and is, for example, wound helically around the acrylic acid vapor pipe or runs parallel thereto.

In a preferred embodiment, the treated crude acrylic acid is separated in a column provided with a circulation vaporizer into a first quantity of vapor comprising acrylic acid and a first residue, the first residue is separated in a film evaporator into a second quantity of vapor comprising acrylic acid and a second residue, the first and second quantities of vapor comprising acrylic acid are combined and condensed to give pure acrylic acid, and the second residue is discarded.

In this embodiment, the column is preferably operated so that the first residue amounts to at least 8% by weight, e.g. from 8 to 30% by weight, preferably from 10 to 25% by weight, of the crude acrylic acid fed to the distillation column. This ensures that the residue has a handleable, not excessively high viscosity. In addition, it has been found that a greater degree of evaporation results in significantly greater fouling on the heat-exchange surfaces of the vaporizer employed for heating the bottom of the column, so that the plant has to be shut down and cleaned at shorter time intervals.

To recover the acrylic acid still present in the first residue, the residue is fed to a film evaporator and a further quantity of vapor comprising acrylic acid is obtained. Wiped film evaporators are particularly useful as film evaporator. In these types, the liquid to be concentrated by evaporation is distributed over a tube wall by means of a rotating arrangement of wipers. Evaporators of the Sambay type are particularly preferred. It has been found that film evaporators display a reduced tendency to suffer from fouling because of their construction and thus allow greater evaporation of the residue without interruption for cleaning than would be possible in the primary distillation column. The first residue is preferably concentrated in the film evaporator to from 35% by weight to 5% by weight, in particular from 10% by weight to 20% by weight.

The second quantity of vapor is combined with the first quantity of vapor, conveniently by recirculating the second quantity of vapor to the distillation column. The second quantity of vapor is advantageously introduced below a droplet precipitator provided in the distillation column and the combined vapors are passed through the droplet precipitator. This manner of operation has the advantage that only one common droplet precipitator is necessary to separate off entrained droplets from the first and second quantities of vapor, which reduces capital costs and the need for cleaning. The residues obtained in the film evaporator, which correspond to, for example, from 0.5 to 5% by weight, generally from 1 to 2% by weight, of the total crude acrylic acid feed, are discarded.

In a preferred embodiment of the process of the present invention, the crude acrylic acid which has been treated with the aldehyde scavenger is heated to from 40 to 110° C., preferably from 50 to 60° C., before being introduced into the distillation column. Heating is conveniently carried out by indirect heat exchange, e.g. by means of a flow-through heat exchanger. Introducing preheated crude acrylic acid into the distillation column has the advantage that a smaller quantity of heat has to be introduced at the bottom of the column via the vaporizer provided for this purpose, which in turn leads to reduced fouling on its heat-exchange surfaces.

In the thermal separation of the crude acrylic acid, it is advantageous to use a dissociation catalyst for ester-like oligomeric acrylic acid, in particular diacrylic acid. Suitable dissociation catalysts are, in particular, acids such as alkylsulfonic and arylsulfonic acids, e.g. dodecylbenzenesulfonic acid or p-toluenesulfonic acid, or bases such as sodium hydroxide or potassium carbonate. The dissociation catalyst is usually used in an amount of from 0.5 to 10 kg per metric ton of crude acrylic acid. The dissociation catalyst can be added to the crude acrylic acid feed or to the feed to the film evaporator.

The vapor comprising acrylic acid is then condensed to give pure acrylic acid. The condensation can be carried out by indirect heat exchange, e.g. in a heat exchanger, or preferably by direct heat exchange, e.g. in a gas cooler, by direct contact with a cooling medium. As cooling medium, preference is given to using pure acrylic acid. The pure acrylic acid used as cooling medium preferably contains a storage polymerization inhibitor, for example one of those mentioned above, in an amount of, for example, from 10 to 2000 ppm, preferably from 25 to 350 ppm. Hydroquinone monomethyl ether is particularly preferred for this purpose. The condensation of the vapor comprising acrylic acid is usually carried out at 45° C. or below, generally at from 20 to 40° C.

Since the formation of polymers cannot be prevented completely even when using a polymerization inhibitor, fouling occurs on plant components such as reactor walls, heat-exchange surfaces, on column trays and in lines and pumps, especially after prolonged running times. The plant or plant components and apparatuses therefore have to be cleaned from time to time. For this purpose, the absorption column, the distillation column, the film evaporator and/or other plant components which come into contact with the reaction gases, the high-boiling liquid laden with acrylic acid, the crude acrylic acid, the vapor comprising acrylic acid, the residues or the pure acrylic acid are treated periodically with an aqueous solution of a base.

Preference is given to emptying the plant component to be cleaned, if appropriate rinsing it with water and treating it with the aqueous solution of a base. According to EP-A 1033359, it is then advantageously rinsed with water. However, it is also possible to use an aqueous solution of an inhibitor in place of water. The water used for rinsing before and after the base treatment is generally deionized water, condensate or mains water. As solution of a base, preference is given to using a 5–25% strength by weight solution of potassium or sodium hydroxide, with sodium hydroxide being preferred. Cleaning with the solution of the base is usually carried out at from 20 to 100° C. for generally from 5 to 20 hours. The type and amount of deposits (fouling) naturally determine the cleaning conditions.

A final rinse with a 0.001–1% strength by weight aqueous solution of a polymerization inhibitor is particularly advantageous. As polymerization inhibitors, preference is given to using phenolic compounds, e.g. hydroquinone, hydroquinone monomethyl ether, tert-butylphenols or nitrosophenols, N-oxyl compounds such as 1-oxyl-2,2,6,6-tetramethylpiperidin-4-ol, methylene blue or mixtures thereof.

If a preliminary rinse with water is carried out, the solution obtained is advantageously introduced into the work-up process for the reaction gases comprising acrylic acid from the gas-phase oxidation. The wastewater from the base treatment is disposed of or worked up and/or wholly or partly reused. In this way, all or part of the aqueous solution of the polymerization inhibitor can advantageously be used a number of times. The final rinse with the inhibitor solution largely prevents polymer formation during start-up of the plant and thus leads to a longer running time of the plant.

The method of cleaning described above is not restricted to plants for preparing acrylic acid, but can also be carried out advantageously in plants for preparing/purifying methacrylic acid and (meth)acrylic esters.

It is particularly advantageous to provide the columns and other apparatus items with fixed rinsing lines via which the aqueous solution of a base, water for preliminary or subsequent rinsing or the aqueous inhibitor solution can be introduced as necessary.

The pure acrylic acid obtained in this way can be used directly for the preparation of absorbent resins, in particular superabsorbents (superabsorbent polymers or SAPs for short). A review of the preparation of SAPs based on acrylic acid may be found in F. L. Buchholtz and A. T. Graham (editors) in "Modern Superabsorbent Technology", pp. 69–117, and the references cited therein.

The preparation of SAPs based on acrylic acid is, as is known, carried out by free-radical polymerization of aqueous monomer solutions which comprise essentially acrylic acid and/or its salts as polymerizable monomers. The polymerization is preferably carried out as a solution or gel polymerization in a homogeneous aqueous phase or as a suspension polymerization in which the aqueous monomer solution forms the disperse phase. The hydrogels obtained in this way are subsequently surface-crosslinked.

The polymerization is advantageously carried out as a solution polymerization utilizing the Trommsdorff-Norrish effect (gel polymerization). For this purpose, an aqueous, generally 10–70% strength by weight and preferably 20–60% strength by weight, solution of a monomer mixture comprising acrylic acid is polymerized in the presence of a substance which forms free radicals and optionally in the presence of a suitable graft base.

In the polymerization process, the monomer mixture comprising acrylic acid is used in partially or fully neutralized form, i.e. the degree of neutralization of all monomers bearing acid groups is in the range from 20 to 100 mol %.

Apart from acrylic acid, the monomer mixture to be polymerized can further comprise other ethylenically unsaturated acids, e.g. methacrylic acid, vinylsulfonic acid, 2-acrylamido-2-methylpropanesulfonic acid, or neutral ethylenically unsaturated monomers, e.g. acrylamide, methacrylamide, N-vinyl amides such as N-vinylformamide, N-vinylacetamide, N-methylvinylacetamide, N-vinylpyrrolidone and N-vinylcaprolactam. The further monomers are usually used in an amount of less than 30% by weight, based on acrylic acid.

In general, crosslinker monomers are concomitantly used, usually in an amount of from 0.01 to 5% by weight, based on acrylic acid. Suitable crosslinkers are N,N'-methylenebisacrylamide, polyethylene glycol diacrylates and polyethylene glycol dimethacrylates, which are in each case derived from polyethylene glycols having a molecular weight of from 106 to 8500, preferably from 400 to 2000, trimethylolpropane tri(meth)acrylate, ethylene glycol di(meth)acrylate, propylene glycol di(meth)acrylate, butanediol di(meth)acrylate, hexanediol di(meth)acrylate, triallylamine, dialkyldiallylammonium halides, divinylbenzene, diallyl phthalate, polyethylene glycol divinyl ethers of polyethylene glycols having a molecular weight of from 106 to 4000, and the like.

Suitable graft bases can be of natural or synthetic origin. They include starches, i.e. native starches selected from the group consisting of maize starch, potato starch, wheat starch, rice starch, tapioca starch, sorghum starch, manioc starch, pea starch or mixtures thereof, modified starches, starch degradation products, e.g oxidatively, enzymatically or hydrolytically degraded starches, dextrins, e.g. dextrins obtained by roasting, and also lower oligosaccharides and polysaccharides, e.g. cyclodextrins having from 4 to 8 glucose units in the ring. Further possible oligosaccharides and polysaccharides are cellulose, starch derivatives and cellulose derivativess. Also suitable are polyvinyl alcohols, homopolymers and copolymers of N-vinylpyrrolidone, polyamines, polyamides, hydrophilic polyesters or polyalkylene oxides, in particular polyethylene oxide and polypropylene oxide.

Polymerization reactors which can be used are the reactors customary for the preparation of polymers; in the case of solution polymerization, preference is given to belt reactors, extruders and kneaders (cf. "Modern Superabsorbent Polymer Technology", Section 3.2.3). The polymers are particularly preferably prepared by a continuous or batchwise kneading process.

Suitable initiators are, for example, peroxo compounds such as organic peroxides, organic hydroperoxides, hydrogen peroxide, persulfates, perborates, azo compounds and redox catalysts.

The polymers are generally obtained as hydrogels. Their moisture content is generally in the range from 20 to 80% by weight. The hydrogel obtained in this way is then converted in a manner known per se into a hydrogel-forming powder and is subsequently surface-crosslinked. For this purpose, the hydrogel obtained in the polymerization is generally firstly comminuted by known methods. The rough comminution of the hydrogels is carried out by means of customary tearing and/or cutting tools. The preferably neutralized or partially neutralized polymer obtained in this way is subsequently heated at, for example, from 80° C. to 250° C. This gives the polymers in the form of powder or granules, which may be subjected to further milling and screening procedures to adjust the particle size.

The subsequent surface crosslinking is carried out in a manner known per se on the resulting, dried, preferably milled and screened polymer particles. Surface crosslinking is carried out using compounds which have at least two functional groups capable of reacting with the functional groups, preferably the carboxyl groups, of the polymer to produce crosslinks (postcrosslinkers). For this purpose, the postcrosslinkers are applied, preferably in the form of an aqueous solution, to the surface of the polymer particles.

Suitable postcrosslinkers are, for example:

Ethylene glycol diglycidyl ether, bischlorohydrin ethers of polyalkylene glycols, alkoxysilyl compounds, polyaziridines, diols and polyols and their esters with carboxylic acids or with carbonic acid, e.g. ethylene carbonate or propylene carbonate, carbonic acid derivatives such as urea, thiourea, guanidine, dicyandiamide, 2-oxazolidinone and its derivatives, bisoxazoline, polyoxazolines, diisocyanates and polyisocyanates, di- and poly-N-methylol compounds such as methylenebis(N-methylolmethacrylamide) or melamine-formaldehyde resins.

If necessary, acid catalysts such as p-toluenesulfonic acid, phosphoric acid, boric acid or ammonium dihydrogen phosphate can be added.

The crosslinker solution is preferably applied by spraying a solution of the crosslinker onto the polymer in conventional reaction mixers or mixing and drying units, for example Patterson-Kelly mixers, DRAIS turbulent mixers, Lödige mixers, screw mixers, pan mixers, fluidized-bed mixers or a Schugi-Mix. After the crosslinker solution has been sprayed onto the polymer, a heat treatment step can follow.

A preferred embodiment of the process of the present invention is described in more detail with the aid of FIG. 1 and the examples below.

FIG. 1 shows a plant suitable for producing pure acrylic acid. The hot reaction gas coming from the propane, propylene and/or acrolein oxidation, which comprises acrylic acid together with water vapor, acrolein, formaldehyde, formic acid, acetic acid, maleic anhydride and inert gases, is fed via line 1 into the absorber column 2. In the absorber column 2, the temperature desired for the absorption is set by means of the liquid circuits 3 which are equipped with heat exchangers 4. The high-boiling liquid is introduced at the top of the absorber column 2 via line 5 and scrubs the acrylic acid from the reaction gases in countercurrent. The constituents of the reaction gas which have not been absorbed leave the absorber column 2 via line 6. The liquid flowing out from the absorber column 2 is conveyed via line 7 through the heat exchanger 8 where it is heated to the top of the desorber column 9. Stripping gas is fed into the desorber column 9 at the bottom via line 10. The stripping gas travels in countercurrent to the downflowing liquid laden with acrylic acid and substantially frees it of volatile impurities. The gas leaving the top of the desorber is conveyed via line 11, if desired also via line 12 or 13, to the absorber column 2.

The liquid flowing out from the bottom of the desorber column 9 is conveyed via line 14 to the distillation column 15. Crude acrylic acid is taken off in the upper region of the distillation column 15 via line 16. Remaining low boilers are removed at the top of the distillation column 15 via line 28. The high-boiling liquid which has been freed of acrylic acid can, if appropriate after work-up, be recirculated after cooling in the heat exchanger 18 to the top of the absorber column 2.

The crude acrylic acid taken off at the top of the distillation column 15 is fed via line 16 to the reaction vessel 19 into which an aldehyde scavenger is metered via line 20. After an appropriate reaction time, the crude acrylic acid is conveyed via line 21 to the column 22 which is free of internals and provided only with a droplet precipitator 23. In a preferred embodiment, a heat exchanger is provided in line 21 to preheat the crude acrylic acid. The vapor comprising acrylic acid which leaves the column 22 is taken off via line 28 and can be condensed to give pure acrylic acid. The high-boiling residue at the bottom of the column 22 is fed via line 24 to an evaporator 25. The vapor obtained is conveyed via line 26 back to the column 22 and fed into the latter below the droplet precipitator 23. The concentrated residue from the evaporator 25 is taken off via line 27 and disposed of.

EXAMPLE 1

In an apparatus as shown in FIG. 1, the hot reaction gases (230° C.) from the oxidation of propene, which had been carried out in a known manner by means of atmospheric oxygen in two stages in the gas phase over multimetal oxide catalysts, were fed via line 1 to the absorber column 2. The column was equipped with 35 bubble cap trays and two external heat exchangers. At the top of the column, 0.7 kg of a solvent mixture comprising 58.8% by weight of diphenyl ether, 21.2% by weight of biphenyl and 20% by weight of dimethyl o-phthalate and containing 0.1% by weight of phenothiazine and having a temperature of 45° C. was fed in (line 5) for every 1000 l of reaction gases. The heat exchangers were operated so that the gas temperature after the 2$^{nd}$ heat exchanger was about 60° C. The liquid comprising acrylic acid which flowed out at the bottom of the column was brought to a temperature of 105° C. by means of the heat exchanger 8 and fed to the desorber column 9 (25 bubble cap trays). 200 l of air heated to 90° C. per kg of liquid from the absorber column were blown at the bottom. The stripping gases laden with low boilers were fed back to the absorption column. The liquid flowing out from the column 9 was fed to the distillation column 15 (43 dual-flow trays, external circulation vaporizer, temperature at the bottom=175° C., pressure at the top=100 mbar) on the 5$^{th}$ tray. Liquid crude acrylic acid was discharged via a side offtake (35$^{th}$ tray); this comprised, inter alia, the following components:

| | |
|---|---|
| Acrylic acid | 99.3% by weight |
| Diacrylic acid | 0.2% by weight |
| Acetic acid | 0.15% by weight |
| Propionic acid | 0.04% by weight |
| Furfurals | 0.4% by weight |
| Benzaldehyde | 0.01% by weight |
| Water | 0.1% by weight |
| Phenothiazine | 0.05% by weight |

The low boilers discharged at the top of the column, mainly water and acetic acid, contained 2% by weight of acrylic acid, and the solvent mixture obtained at the bottom of the column contained about 1% by weight of acrylic acid and was recirculated to the absorption column. The crude acrylic acid was treated in a stirred vessel (19) with the double molar amount (based on furfural and benzaldehyde) of aminoguanidine hydrogen carbonate at 23° C. for 10 hours. The mixture was subsequently heated to 50° C., admixed with 0.3% by weight of dodecylbenzenesulfonic acid and fed to the bottom of the distillation column 22. The column was equipped with a spray precipitator (23) and a circulation vaporizer. The temperature at the bottom was 85° C., and the pressure was 90 mbar. The gaseous acrylic acid discharged was condensed by quenching with liquid acrylic acid and was stabilized by addition of 200 ppm of hydroquinone monomethyl ether (MEHQ). For this purpose, an about 1.5% strength by weight solution of MEHQ in acrylic acid was continuously metered in in the required amount.

The acrylic acid remaining in the bottom product (15% by weight of the feed) was mostly distilled off in a Sambay evaporator (25) (75° C., 70 mbar), and the vapor was introduced into the column (22) below the spray precipitator (23).

The condensed pure acrylic acid had the following composition:

| | |
|---|---|
| Acrylic acid | 99.7% by weight |
| Diacrylic acid | 0.01% by weight |
| Acetic acid | 0.14% by weight |
| Propionic acid | 0.04% by weight |
| Aldehydes | <5 ppm |
| Phenothiazine | <1 ppm |
| Water | 0.11% by weight |

The bottoms from the Sambay distillation (about 2% by weight of the feed to column 22) contained about 20% by weight of acrylic acid and were disposed of. About 99% by weight of the acrylic acid present in the crude acrylic acid were recovered. The distillation unit could be operated without problems for more than 30 days.

A 40% strength aqueous solution of the pure acrylic acid was prepared and neutralized with sodium hydroxide. The solution was admixed with 0.50% by weight, based on acrylic acid, of crosslinker (diacrylate of a polyethylene glycol having a mean molecular weight of 400). As initiator, the following system was employed:
0.005% by weight of hydrogen peroxide and
0.006% by weight of ascorbic acid and
0.28% by weight of sodium peroxodisulfate, based on acrylic acid.

The individual components of this reaction solution (dilute aqueous solutions of hydrogen peroxide, ascorbic acid, sodium peroxodisulfate and the monomer/crosslinker solution) were metered separately into a kneader as reactor and mixed while running into the reactor with the polymerization starting quickly even during mixing.

600 kg/h of reaction solution were introduced and the gel produced by polymerization in the kneader was discharged continuously. The temperature of the cooling water in the reactor jacket was regulated to 90° C. During the polymerization, 14 m$^3$/h of nitrogen were passed through the kneader as inert gas. The reaction volume was 300 l.

The gel which had been discharged was dried, milled and screened to produce a particle size fraction of 100–800 µm.

The invention claimed is:

1. A process for preparing water-absorbent resins, which comprises:
   a) obtaining crude acrylic acid by either
      a1) absorbing acrylic acid from the reaction gases obtained from the catalytic gas-phase oxidation of propane, propylene and/or acrolein in an absorption liquid and isolating crude acrylic acid from the absorption liquid laden with acrylic acid,
   or
      a2) separating a crude acrylic acid fraction from said reaction gases by fractional condensation and, optionally, purifying the condensed fraction of acrylic acid by crystallization,
   b) treating the crude acrylic acid obtained from a1) or a2) with an aldehyde scavenger,
   c) separating pure acrylic acid from the treated crude acrylic acid by distillation, and
   d) polymerizing the pure acrylic acid, optionally after partial neutralization, alone or in admixture with other ethylenically unsaturated monomers, under free-radical polymerization conditions,
   wherein the isolation of the pure acrylic acid by distillation is conducted without reflux of condensate by thermally separating the treated crude acrylic acid into vapor comprising acrylic acid and a residue and quantitatively condensing the vapor to obtain pure acrylic acid, no fraction boiling lower than the pure acrylic acid fraction being isolated.

2. The process as claimed in claim 1, wherein the absorption liquid laden with acrylic acid is stripped by means of a stripping gas to remove volatile impurities.

3. The process as claimed in claim 1, wherein the aldehyde scavenger is aminoguanidine hydrogen carbonate.

4. The process as claimed in claim 1, wherein the treated crude acrylic acid is separated in a column provided with a circulation vaporizer into a first quantity of vapor comprising acrylic acid and a first residue, the first residue is separated in a film evaporator into a second quantity of vapor comprising acrylic acid and a second residue, the first and second quantities of vapor comprising acrylic acid are combined and condensed to give pure acrylic acid, and the second residue is discarded.

5. A process as claimed in claim 1, wherein the absorption liquid contains a polymerization inhibitor.

6. A process as claimed in claim 1, wherein the absorption liquid is diphenyl ether, biphenyl, dimethyl o-phthalate or a mixture thereof.

7. The process as claimed in claim 1, wherein the aldehyde scavenger, is aminoguanidine hydrogen carbonate.

8. The process as claimed in claim 2, wherein the treated crude acrylic acid is separated in a column provided with a circulation vaporizer into a first quantity of vapor comprising acrylic acid and a first residue, the first residue is separated in a film evaporator into a second quantity of vapor comprising acrylic acid and a second residue, the first and second quantities of vapor comprising acrylic acid are combined and condensed to give pure acrylic acid, and the second residue is discarded.

9. The process as claimed in claim 3, wherein the treated crude acrylic acid is separated in a column provided with a circulation vaporizer into a first quantity of vapor comprising acrylic acid and a first residue, the first residue is separated in a film evaporator into a second quantity of vapor comprising acrylic acid and a second residue, the first and second quantities of vapor comprising acrylic acid are combined and condensed to give pure acrylic acid, and the second residue is discarded.

10. The process as claimed in claim 2, wherein the absorption liquid contains a polymerization inhibitor.

11. The process as claimed in claim 3, wherein the absorption liquid contains a polymerization inhibitor.

12. The process as claimed in claim 4, wherein the absorption liquid contains a polymerization inhibitor.

13. The process as claimed in claim 2, wherein the absorption liquid, is diphenyl ether, biphenyl, dimethyl o-phthalate or a mixture thereof.

14. The process as claimed in claim 3, wherein the absorption liquid, is diphenyl ether, biphenyl, dimethyl o-phthalate or a mixture thereof.

15. The process as claimed in claim 2, wherein the absorption liquid, is diphenyl ether, biphenyl, dimethyl o-phthalate or a mixture thereof.

16. The process as claimed in claim 2, wherein the absorption liquid, is diphenyl ether, biphenyl, dimethyl o-phthalate or a mixture thereof.

17. The process as claimed in claim 1, wherein acrylic acid is separated from the absorbing liquid by a stripping gas in a column.

* * * * *